United States Patent [19]

Wexler et al.

[11] 4,323,710
[45] Apr. 6, 1982

[54] PARTIAL ALKYLATION OF POLYHYDROXYBENZOPHENONES

[75] Inventors: Allan Wexler, Haledon; Paritosh M. Chakrabarti, Cedar Grove; Michael J. Brown, Randolph, all of N.J.

[73] Assignee: GAF Corporation, New York, N.Y.

[21] Appl. No.: 203,026

[22] Filed: Nov. 3, 1980

[51] Int. Cl.$^3$ .............................................. C07C 45/61
[52] U.S. Cl. .................................................. 568/315
[58] Field of Search ........................ 568/315, 322, 333

[56] References Cited

U.S. PATENT DOCUMENTS

| | | | |
|---|---|---|---|
| 2,773,903 | 12/1956 | Hardy et al. | 568/322 |
| 2,777,828 | 1/1957 | Day et al. | 568/333 |
| 2,861,053 | 11/1958 | Lappin et al. | 568/333 |
| 3,005,959 | 10/1961 | Armitage | 260/45.95 R |
| 3,098,842 | 7/1963 | Armitage | 260/45.95 R |
| 3,584,053 | 6/1971 | Bobali et al. | 568/315 |
| 3,632,650 | 1/1972 | Hechenbleikner et al. | 568/315 |
| 3,639,483 | 2/1972 | Shioda et al. | 568/315 |
| 3,697,599 | 10/1972 | Dabley | 568/315 |
| 3,923,901 | 12/1975 | Battin et al. | 568/315 |

FOREIGN PATENT DOCUMENTS 1167679 10/1969 United Kingdom ................ 568/322

OTHER PUBLICATIONS

Schonfeldt, Surface Active Ethylene Oxide Adducts, pp. 135–175, Pargamon Press (1970).

*Primary Examiner*—Natalie Trousof
*Assistant Examiner*—James H. Reamer
*Attorney, Agent, or Firm*—James Magee, Jr.; Walter Katz

[57] ABSTRACT

The partial alkylation of a polyhydroxybenzophenone having ortho- and para-hydroxy substituents to form an ortho-hydroxy, para-alkoxy benzophenone is carried out in the presence of a non-aqueous solvent, viz. a polyethylene glycol or its mono or dialkylated derivatives, whereby high yields of alkylated product are obtained in shorter reaction times.

7 Claims, No Drawings

PARTIAL ALKYLATION OF POLYHYDROXYBENZOPHENONES

BACKGROUND OF THE INVENTION

Related Applications

Ser. No. 199,418, filed Oct. 22, 1980, describes and claims a process of alkylation of carboxylate salts using a polyoxyethylene nonionic surfactant for the reaction.

Field of the Invention

This invention relates to an improved process for the alkylation of hydroxybenzophenones.

DESCRIPTION OF THE PRIOR ART

It is well known that certain benzophenones substituted with hydroxy and alkoxy groups are useful as ultraviolet light absorbers in various compositions. Furthermore, it is well known that such ultraviolet light absorber compounds must contain at least one hydroxy group ortho to the carbonyl group of the benzophenone. Such compounds are described, for example, in the following U.S. Pat. Nos. Day et al., 2,777,828; Armitage et al., 3,005,959 and 3,098,842; and Lappin et al., 2,861,053. In application, these compounds are particularly useful as light stabilizers in resinous compositions, such as polyolefins, particularly polypropylene; unsaturated polyester resins; and other resinous compositions of various types, such as polyvinyl chloride, styrene polymers, styrene-acrylonitrile copolymers, polyacrylates, and the like.

The o-hydroxy, p-alkoxybenzophenones prepared by the improved process of this invention have been prepared in several ways in the past. One such method has been described by Hardy et al., U.S. Pat. No. 2,773,903, in which a suitable benzoyl chloride is reacted with a dialkoxy benzene in the presence of a stoichiometric amount of AlCl$_3$ and small amounts of dimethylformamide. Upon heating the reaction mixture after the initial reaction, the alkoxy group ortho to the carbonyl group undergoes a dealkylation to restore the hydroxy group. The process has certain deficiencies due to the unavailability of starting materials for the preparation of some of the most desirable compositions. Preparation of such intermediates would involve extra steps to the process and add to the cost.

Another method which has been used is the direct alkylation of hydroxybenzophenones to the desired hydroxyalkoxybenzophenones with alkyl bromides. See U.S. Pat. No. 2,861,053. Use of alkyl bromides was necessary because the more readily available and less expensive alkyl chlorides, having a lower degree of reactivity, required lengthy reaction times to achieve only mediocre yields of the desired products. These alkylation reactions were conducted in solvents such as acetone, sec. butanol, or isopropanol.

British Pat. No. 1,167,679 describes the preparation of these compounds in an aliphatic ketone using an inorganic iodide catalyst. In this process the yields of product are low. Although the yields of desired products using an alkyl bromide have been adequate, the process has involved lengthy reaction times (15 hours and more) and certain tedious recovery techniques, such as filtrate concentration, and, in some cases, recrystallization, to achieve optimum product purity. Moreover, the process is expensive for the reasons previously stated.

Still another method which has been used is the direct alkylation of hydroxybenzophenone in mono lower alkyl ethers of ethylene glycol and diethylene glycol as a solvent. See U.S. Pat. No. 3,923,901. However, even in these solvents, the rate of reaction and yields leave something to be desired, e.g. in a rather extended reaction period of 5 hours an average yield of only about 85% is obtained.

In U.S. Pat. No. 3,697,599 there is described an aqueous process for preparing alkylated hydroxybenzophenones. In this process, an aqueous solution of an alkali metal hydroxide and a surfactant is used as a solvent system for the reaction of 2,4-dihydroxybenzophenones with an alkyl halide. As with the prior processes, however, the reaction period extends from 8 to 16 hours and the yields are low, i.e. from 50 to 85%.

What is needed, therefore, is an improved process for making such compounds, in which the alkyl halides, particularly the alkyl chlorides, can be used effectively, i.e., in which the reaction time is reduced and a high yield of pure alkylated product is obtained. It is the object of this invention to provide such a process.

SUMMARY OF THE INVENTION

What is described herein is an improved process for the partial alkylation of polyhydroxybenzophenones having both ortho- and para-hydroxy substituents and repesented by the formula:

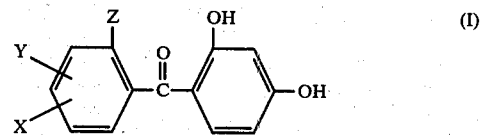

where Z is hydrogen, alkyl, alkoxy, halogen, carboxy, carbalkoxy, or hydroxy and where X and Y individually are hydrogen, alkyl, alkoxy, halogen, carboxy, carbalkoxy or hydroxy, provided that where either X or Y is hydroxy, the other is not hydroxy, to form ortho-hydroxy, para-alkoxybenzophenones of the formula:

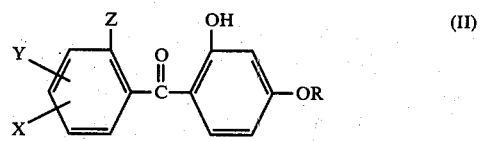

where R is alkyl, Z is as defined above, and X and Y are hydrogen, alkyl, alkoxy, halogen, carboxy, or carbalkoxy, by reaction with an alkyl halide, wherein the improvement comprises carrying out the reaction in the presence of a non-aqueous solvent selected from a polyethylene glycol or its mono or dialkylated derivatives, wherein said material serves as a solid-liquid phase transfer agent for the reaction.

We now find that the rate of the reaction markedly increases with an increase in the oxyethylene content of the solvent. With nine oxyethylene units, for example, the reaction time is reduced to under two hours with a >90% yield of product.

As features of this invention, the solvent used herein is inexpensive as compared to those used previously, the reaction time is reduced substantially, and an exceedingly high yield of pure alkylated product is obtained from the reaction mixture.

DETAILED DESCRIPTION OF THE INVENTION

The non-aqueous solvent used in the improved process of this invention is a polyethylene glycol or its mono or dialkylated derivatives. In the non-aqueous reaction system herein, where there are present two phases, namely, a solid and a liquid phase, the solvent of this invention functions as a solid-liquid phase transfer agent to improve the yield and shorten the reaction time of the alkylation.

In carrying out the process of the invention, a reaction mixture comprising the appropriate polyhydroxybenzophenone and alkyl halide reactants, an alkali acid acceptor, metal bromide or iodide catalyst (if used) and the solvent, are heated to reflux while distilling off any water which may be present and that which may be formed in the reaction. After a suitable reaction time, which in this invention is 2 hours or less, a small amount of sodium hydrosulfite is added, if desired, to reduce the color. Alternatively, zinc dust and phosphoric acid may be used to reduce color bodies. The mixture is then filtered, the filter cake is washed with solvent and the combined filtrates are cooled to 25°–30° C. Crystallization is allowed to proceed with agitation at this temperature for about 30 minutes, and then cooled to 0°–5° C. The product is isolated by filtration and dried.

Among the hydroxybenzophenones of general formula I which may be used in accordance with the process of this invention are included:

2,4-dihydroxybenzophenone
2,2′,4-trihydroxybenzophenone
2,2′,4-trihydroxy-4′-methylbenzophenone
2,2′,4-trihydroxy-4′-methoxybenzophenone
2,2′,4-trihydroxy-4′-chlorobenzophenone
2,4-dihydroxy-4′-tert. butylbenzophenone
2,4-dihydroxy-4′-methylbenzophenone
2,4-dihydroxy-4′-chlorobenzophenone
2,4-dihydroxy-3′,5′-dimethylbenzophenone
2,4-dihydroxy-3′,5′-dimethoxybenzophenone
2,4-dihydroxy-3′,5′-dichlorobenzophenone
2,2′,4,4′-tetrahydroxybenzophenone
2-carboxy-4,4′-dihydroxybenzophenone
3-carbethoxy-2′,4′-dihydroxybenzophenone Although the above are representative members of the class of hydroxybenzophenones which are useful in the present invention, the invention should not be restricted to them. The hydroxybenzophenones are generally conveniently prepared by a Friedel-Crafts ketone synthesis similar to that used in Hardy et al., cited above, or by the condensation of benzotrichloride with resorcinol. The alkyl halides which may be used as alkylating agents in the invention are those containing up to 20 carbon atoms, for example, methyl chloride, 1-chloropropane, octadecyl chloride, octyl chloride, dodecyl chloride, eicosyl chloride, and the corresponding bromides and iodides.

The invention is most advantageously, and preferably, practiced using the alkyl chlorides as alkylating agents, although it is equally applicable to the alkyl bromides and iodides.

While the alkylation reaction can be conducted using stoichiometric amounts of the alkyl halide and hydroxybenzophenone, it is preferred to use an excess of the alkyl halide, i.e., up to about 25% over that required, preferably no more than about 10%.

As the alkali acid acceptor an alkali metal carbonate, bicarbonate or hydroxide is used in slight excess over that required. Sodium or potassium carbonates are preferred.

From about 0.1% to about 3% of the metal bromide or iodide may be used as catalyst for the alkylation reaction.

Suitable poly(ethylene glycol)s include those having the formula:

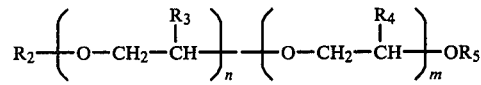

where n=3–10,
m=0–30
$R_2$ and $R_5$ are hydrogen, and
$R_3$ and $R_4$ are independently hydrogen or alkyl of 1–2 carbon atoms.

Suitable poly(ethylene glycol)s (PEG's) are compounds whose average molecular weight ranges from $\overline{MW}$ 200 to $\overline{MW}$ 1000.

Suitable monoalkylated derivatives of the above formula include compounds where:

n=1–10, m=0–30, $R_2$ is alkyl having from 4–30 carbon atoms, aryl and alkaryl having from 6–30 carbon atoms, and, $R_3$ and $R_4$ are independently hydrogen or alkyl having 1–2 carbon atoms.

Representative monoalkylated derivatives include polyoxyethylene nonionic surfactants, such as the ethoxylated alkylphenols, e.g. the Igepal ® surfactants, sold by GAF Corp. as, for example, Igepal CO-630, which is nonylphenoxypoly (ethyleneoxy)9ethanol, OD-410, which is phenoxyoxypoly(ethyleneoxy)1 ethanol, and CA-420, which is octylphenoxypoly(ethyleneoxy)3ethanol, DM-530, which is a dialkylphenoxypoly(ethyleneoxy)ethanol; the aliphatic polyethers, e.g. the Antarox ® surfactants, sold by GAF Corp. as, for example, Antarox BL-214 and BL-240; and polyoxyethylated alcohols, e.g. Emulphogene ® surfactants, sold by GAF Corp. as, for example, Emulphogene BC-420, which is tridecyloxypoly(ethyleneoxy)ethanol, and DA-530, which is polyoxyethylated (4) decyl alcohol.

Suitable dialkylated derivatives include compounds where: n=1–10, m=0–30, $R_2$ and $R_5$ are alkyl having from 1–10 carbon atoms, and $R_3$ and $R_4$ are independently hydrogen or alkyl having from 1–2 carbon atoms, as for example, triethylene glycol dimethyl ether, tetraethylene glycol dimethyl ether, hexaethylene glycol dimethyl ether and the like.

In the best mode of the invention, the solvent is Igepal CO-630; it affords not only the highest yield of pure product in the shortest reaction time, but it is a quite inexpensive solvent, may be recycled at least 15 times and can dissolve large amounts of the reactants per batch.

The invention will now be described more fully in the following examples.

EXAMPLE 1

SYNTHESIS OF 2-HYDROXY-4-OCTYLOXY-BENZOPHENONE

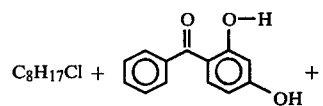

-continued

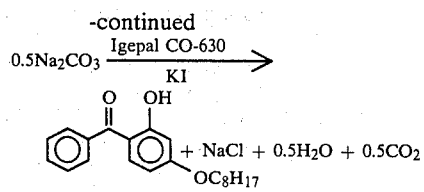

To a 250 ml 3-neck round bottom flask is charged 21.4 g of 2,4-dihydroxybenzophenone, 16.3 g of octyl chloride, 5.6 g of sodium carbonate, 0.664 g of potassium iodide, and 21.4 g of Igepal CO-630. The mixture is heated to 155° C. with vigorous stirring. Sufficient water, generated by the reaction, is distilled out to allow the reaction to reach temperature; any co-distilling octyl chloride (upper layer) is returned to the reactor. The reaction is then kept at 155° C. for 2 hours. Thereafter excess octyl chloride and water are recovered at 11 mm and 155° C.; which about 15 minutes is required to recover 0.7 g of a cloudy yellow liquid. The reactor then is cooled to 45° C. and 30 ml of acetone is added to precipitate salts and facilitate filtration. The mixture is filtered through a warm fitted glass funnel and the salt cake is washed once with 20 ml of acetone. The acetone in the filtrate is recovered in vacuo for recycle, initially at a pot T=80° C. at 18-23" of Hg and finally at 110° C. and 11 mm. The filtrate, containing surfactant and product, a volume of 40 ml is diluted with 85 ml of methanol and cooled to $-8°$ C. to precipitate the product, which is filtered and washed twice with 40 ml of $-8°$ C. methanol. The product is sucked dry for 5 minutes and then used in the next step. From the filtrate, methanol and surfactant are recovered for recycle.

A vacuum dried sample is used for yield. The yield=30.4 g, 93.3%.

EXAMPLE 2

Following the procedure of Example 1, except for the use of the listed surfactants in the Table 1 in place of Igepal CO-630, there is produced the desired product in the yields indicated.

| SOLVENT | % YIELD |
| --- | --- |
| Antarox BL-214 | 89 |
| Antarox BL-240 | 80 |
| Igepal OD-410 | 90 |
| Igepal CA-420 | 90 |
| Emulphogene BC-420 | 90 |
| Agent 100-H (phenol + 6 EO) | 91 |
| Phenol + 2 EO | 92 |

EXAMPLE 3

Following the procedure of Example 1, except for the use of PEG-400 [poly(ethylene glycol)-$\overline{MW}$=400], in the place of Igepal CO-630, there is produced the desired product in comparable yield.

EXAMPLE 4

Following the procedure of Example 1, except for the use of hexaglyme (hexaethylene glycol dimethyl ether) in the place of Igepal CO-630 there is produced the desired product in comparable yield.

What is claimed is:

1. The process for alkylating a polyhydroxybenzophenone of the formula:

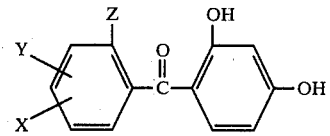

where Z is hydrogen, alkyl, alkoxy, halogen or hydroxy and where X and Y individually are hydrogen, alkyl, alkoxy or halogen to produce an ortho hydroxy, para alkoxybenzophenone of the formula:

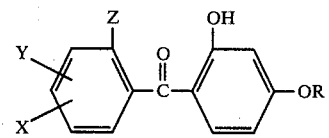

where R is alkyl and Z and X and Y are as defined above;
which comprises the steps of:
(a) forming a reaction mixture consisting of said polyhydroxybenzophenone, an alkyl chloride, a metal bromide or iodide catalyst, a solid acid acceptor, and a non-aqueous solvent consisting of a polyethylene glycol or its mono- or dialkylated derivatives,
(b) heating the reaction mixture to a reaction temperature of about 155° C. and refluxing the mixture whereupon the reaction is effected from two phases only, namely, a solid and liquid solvent phase in which the solvent also functions as a solid-liquid phase transfer catalyst to improve the yield of product and shorten the reaction time,
(c) removing any water of reaction at said reaction temperature,
(d) continuing to reflux for a time sufficient to effect alkylation, and,
(e) recovering the alkylated product.

2. The process of claim 1 wherein the yield of isolated product of high purity is at least 90% for a period of 2 hours or less.

3. The process according to claim 1 further characterized in that said solvent is selected from polyethylene glycol and its mono and dialkyl substituted derivatives.

4. The process according to claim 1 wherein said polyethylene glycol has the formula:

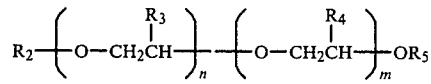

where
n=3-10,
m=0-30,
$R_2$ and $R_5$ are hydrogen, and,
$R_3$ and $R_4$ are independently hydrogen or alkyl of 1-2 carbon atoms.

5. The process according to claim 1 wherein said monoalkyl substituted derivatives of polyethylene glycol has the formula of claim 4 where:
n=1-10,
m=0-30,
$R_2$ is alkyl having from 4-30 carbon atoms, aryl and alkaryl having from 6-30 carbon atoms, and, $R_3$ and $R_4$ are independently hydrogen or alkyl having 1–2 carbon atoms.

6. The process according to claim 1 wherein said dialkyl substituted derivatives of polyethylene glycol has the formula of claim 4 where:

n = 1–10,
m = 0–30, $R_2$ and $R_5$ are alkyl having from 1–10 carbon atoms, and, $R_3$ and $R_4$ are independently hydrogen or alkyl having 1–2 carbon atoms.

7. The process according to claim 1 wherein said acid acceptor is solid sodium carbonate.

* * * * *